United States Patent [19]

Kirsch

[11] Patent Number: Plant 6,174

[45] Date of Patent: May 10, 1988

[54] LILY PLANT NAMED HALEY

[75] Inventor: Ted T. Kirsch, Myrtle Point, Oreg.

[73] Assignee: Melridge Inc., Gresham, Oreg.

[21] Appl. No.: 861,243

[22] Filed: May 8, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler; W. Dennis Drehkoff

[57] ABSTRACT

A new and distinct variety of Oriental hybrid lily cultivar characterized particularly by its medium height and large, semi-upright to outward facing flowers of rich magenta rose coloration carried on ascending pedicels forming a compact raceme, flowering profusely in late July under field conditions in northern California and western Oregon and having a vigorous growth habit.

1 Drawing Sheet

BACKGROUND OF THE INVENTION

This new variety of lily plant originated as a seedling of unknown parentage discovered by me at my nursery at Arcata, Calif. Its very large and richly colored flowers promted me to propagate this new plant for further evaluation by bulb scale propagation methods with very satisfactory results. Successive generations of this new plant produced by propagation from bulblets and division, as well as by tissue culture originating from bulb scales, have demonstrated that the novel and distinctive characteristics of this new lily variety hold true from generation to generation and appear to be firmly fixed.

This new plant retains its large flower size and ascending pedicels, as well as good flower and bud color, when forced into flower out of season. Bulbs which have been dug at the proper stage of maturity and are properly precooled can be forced into flower out of season with a reliable performance, even during periods of relatively low light.

DESCRIPTION OF THE DRAWING

This new variety of lily plant is illustrated by the accompanying photographic drawing, which shows the form and coloration of its large, bowl-shaped flowers, the color rendition being as nearly true as can be reasonably obtained by conventional photographic procedures.

DESCRIPTION OF THE NEW VARIETY

The following is a detailed description of my new variety of Oriental hybrid lily, with nomenclature according to The International Lily Register (The Royal Horticultural Society, London, 1969), and with color designations according to The R.H.S. Colour Chart published in 1966. The observations were made on greenhouse grown plants at Sandy, Oreg., in the spring of 1985, and on field grown plants at Arcata, Calif., in the summer of 1985.

THE PLANT

Origin: Seedling.

Parentage: Unknown.

Classification:

*Botanic.*—Hybrid lilium cultivar, Division VII-B of The Horticultural Classification of Lilies (The Royal Horticultural Society, 1969).

*Commercial.*—Oriental Hybrid Lily.

Form: Single stem, erect and bushy.

Height: 69 to 90 cm.

Growth: Compact, sturdy and vigorous.

Foliage:

*Quantity.*—Abundant.

*Leaf size.*—Ranging from 12 cm. long and 3 cm. wide at the top of the stem to 5 cm. long and 2 cm. wide at the bottom of the stem.

*Leaf shape.*—Broad lanceolate.

*Texture.*—Leathery.

*Aspect.*—Glossy.

*Color.*—Dark green (chlorophyll pigmentation overlaid with anthocyanin).

Bulbs:

*Size.*—Up to 30 cm. in circumference depending upon age.

*Color.*—White, with flushes of soft pink or yellow which deepen as the bulbs become larger or are exposed to light.

THE BUD

Form: Ovate with obtuse tip.

Size: About 10 to 12 cm. long and about 10 cm. in circumference, depending upon light and nutritional levels.

Opening rate: The bud opens slowly in response to morning light; the buds open successively from the lowermost to the uppermost as is typical with lilium.

Color: The buds are basically cream-white to softest pink with ribs of medium magenta rose 63C-D just before the buds open, the base color shading to a softer tone at the tips of the buds.

Peduncle:

*Length.*—About 2 to 3 cm.; may elongate under low light conditions or when bulbs have been improperly stored prior to forcing.

*Color.*—Dark green.

THE FLOWER

Blooming habit: The flowers bloom profusely and once in midseason, flowering late in July under field conditions at Arcata, Calif. This plant will flower in 95 to 110 days in greenhouse when properly forced from appropriately precooled bulbs.

Size: Large; averaging 18 to 20 cm. in diameter, the tepals recurving to provide a bloom 15 to 16 cm.

wide. The recurved tepals form a bowl about 3.5 to 4.5 cm. deep.

Borne: In a compact raceme with each pedicel bearing one bud. Bulbs of typical commercial size bear an average of five to eight flowers.

Shape: Generally bowl-shaped with broad tepals, slightly recurved and in hexagonal Tepalage:

*Number.*—Six.

*Arrangement.*—Imbricated.

*Form.*—The tepals are generally ovate with the inner tepals averaging about 6 cm. wide and the outer tepals averaging about 3 cm. wide. The inner tepals overlap only slightly and, in general, the tepalage arrangement is very regular.

*Color.*—The basic color is red purple 63A-B with a deeper band of 53B about 2 to 3 mm. wide along the midrib shading through 63A-B to 63C along the margin, which is white, the white margin tapering from about 4 to 5 mm. wide at the tepal apex to about 1 mm. wide at the base. The tepal margins are only slightly frilled and the nectaries are green with a yellow margin about 1 to 2 mm. wide. The papillae are 63B in color and are distributed over the entire colored area of the tepals.

*Color change.*—The basic color fades slightly and becomes more brown as the flower ages or in intense light and heat. Under cool conditions, the color is richer and retained longer.

*Tepal longevity.*—The tepals stay on the stem about two to three weeks.

Pedicel:

*Length.*—About 7 to 8 cm.

*Color.*—Dark green, ascending at a 45° angle from the stem.

Disease resistance: The flower and the plant appear to be adequately resistent to disease as observed at Sandy, Oreg., and at Arcata, Calif.

Fragrance: The fragrance is heavy and sweet.

Lasting quality: The flower is long lasting on both field grown plants and forced potted specimens.

REPRODUCTIVE ORGANS

Stamens:

*Number.*—Six.

*Arrangement.*—Typical of genus lilium.

Anthers:

*Length.*—About 20 mm.

*Color.*—Greyed red 179A-B.

Filaments:

*Length.*—About 7 to 8 cm.

*Color.*—Soft green to white.

Pistils:

*Number.*—One per flower.

Stigma:

*Size.*—Large.

*Color.*—Soft purple-grey.

Style:

*Color.*—Light green to white, sometimes slightly pink.

Ovary: Typical of genus lilium.

I claim:

1. A new and distinct variety of hybrid Oriental lily, substantially as herein shown and described, characterized by its outwardly facing, richly colored flowers of large size, good substance and form, in a raceme of ascending pedicels, and by its vigorous growth habit and medium height.

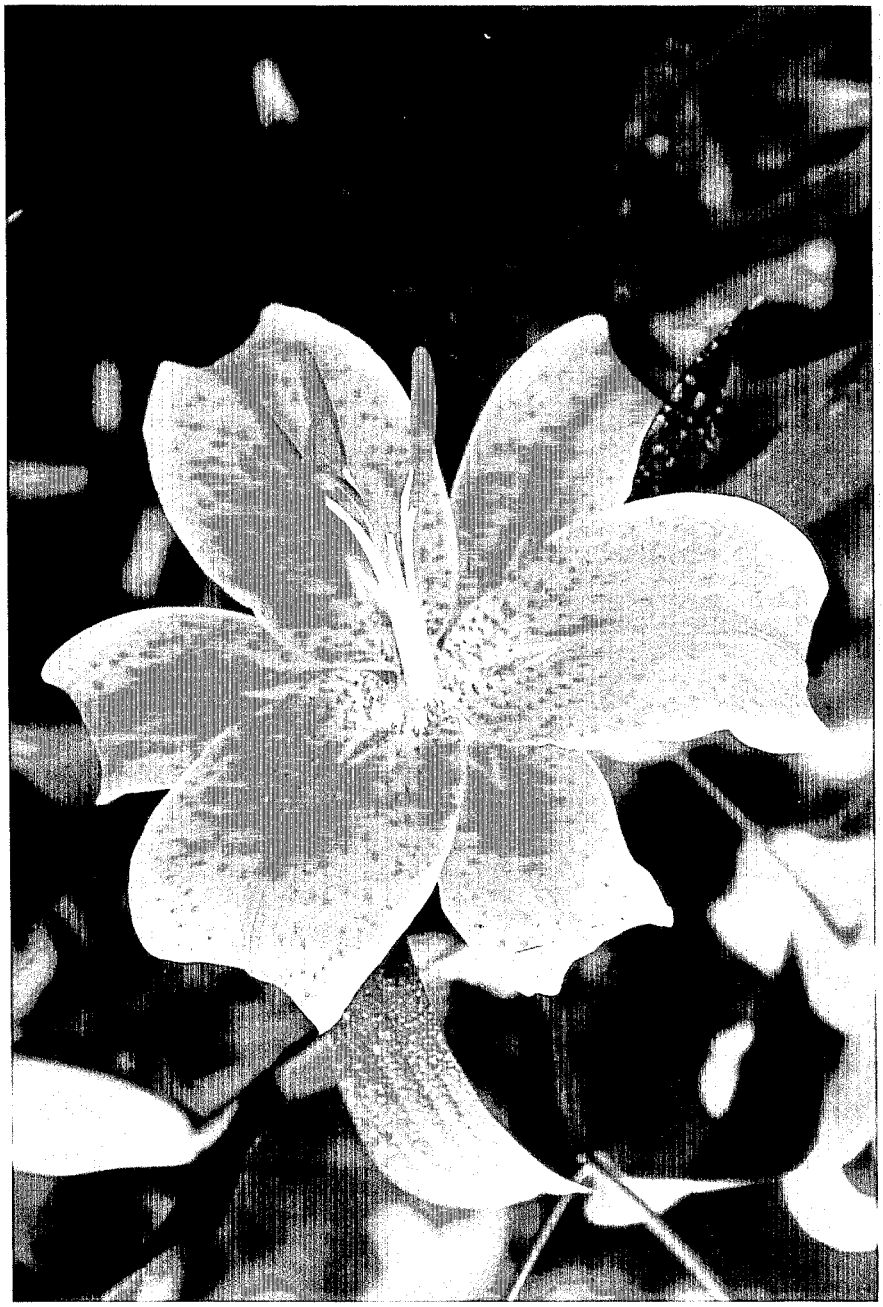

* * * * *